United States Patent [19]

Tyagi

[11] Patent Number: 5,807,674
[45] Date of Patent: Sep. 15, 1998

[54] DIAGNOSTIC ASSAYS AND KITS FOR RNA USING RNA BINARY PROBES AND A PROTEIN THAT IS AN RNA-DIRECTED RNA LIGASE

[75] Inventor: Sanjay Tyagi, New York, N.Y.

[73] Assignee: The Public Health Research Institute of New York, Inc., New York, N.Y.

[21] Appl. No.: 355,438

[22] Filed: Dec. 12, 1994

Related U.S. Application Data

[63] Continuation of Ser. No. 4,993, Jan. 15, 1993, abandoned.
[51] Int. Cl.$^6$ .............................. C12Q 1/68; C12P 19/34; C07H 21/04
[52] U.S. Cl. ........................ 435/6; 435/912; 435/91.21; 435/91.31; 435/91.51; 435/91.52; 435/810; 536/24.32; 536/24.31; 935/16; 935/17; 935/78
[58] Field of Search ........................... 435/6, 91.2, 91.51, 435/91.52, 91.31, 810, 91.21; 536/24.3; 935/77.78

[56] References Cited

U.S. PATENT DOCUMENTS 4,988,617  1/1991  Landegren et al. .................... 435/6

FOREIGN PATENT DOCUMENTS 0439182  7/1991  European Pat. Off. .
481704   4/1992  European Pat. Off. .
9212261  7/1992  WIPO .

OTHER PUBLICATIONS

HJ Blok "Target–Dependent Amplifiable Nucleic Acid Hybridization Probes," a thesis Jun. 2, 1992.
Pritchard et al Anal Biol Clin (1990) 48:492–497.
Sambrook et al, Molecular Cloning: A Laboratory Manual, $2^{nd}$ Ed, 1989, ColdSpring Harbor Laboratory Press, Cold-Spring Harbor, NY, pp. 5.63–5.64.
Barany, F., Genetic Disease Detection and DNA Amplification Using Cloned Thermostable Ligase, Proc. Natl. Acad. Sci. U.S.A. (1991) 88:189–193.
Doudna, J.A. and Szostak, J.W. (1989) RNA–catalysed Snythesis of Complementary–Strand RNA. Nature 339:519–522.

(List continued on next page.)

Primary Examiner—W. Gary Jones
Assistant Examiner—Carla Myers
Attorney, Agent, or Firm—Fish & Richardson P.C.

[57] ABSTRACT

There are provided nucleic acid hybridization assays for RNA targets using RNA binary probes and a protein that is an RNA-directed RNA ligase. Preferred assays include generation of an exponentially amplified signal. Most preferred assays include T4 DNA ligase as the RNA-directed RNA ligase. Also provided are kits for performing assays according to this invention.

39 Claims, 7 Drawing Sheets

OTHER PUBLICATIONS

Fareed, G.C., Wilt, E.M., and Richardson, C.C. (1971) Enzymatic Breakage and Joining of Deoxyribonucleic Acid. The Journal of Bio. Chm., 4:925–932.

Green, R. and Szostak, J.W., Selection of a Ribozyme that Functions as a Superior Template in a Self–Copying Reaction. Science, 1992: 258:1910–1915.

Hunsaker, W.R., Badri, H., Lombardo, M. and Collins, M.L. (1989) Nucleic Acid Hybridization Assays Employing dA–Tailed Capture Probes. II. Advanced Multiple Capture Methods. Anal. Biochem. 181:360–370.

Kleppe, K., van de Sande, J.H., and Khorana, H.G. Polynucleotide Ligase–Catalyzed Joining of Deoxyribo–oligonucleotides on Ribopolynucleotide Templates and of Ribo–ogligonucleotides on Deoxyribopolynucleotide Templates. Proc. of Natl Acad. of Sci., 1970, 67/1:68–73.

Landegren, U., Kaiser, R., Sanders, J., and Hood, L. (1988) A Ligase–Mediated Gene Detection Technique. Science 241:1077–1080.

Lizardi, P., Guerra, C.E., Lomeli, H., Tussie–Luna, I., and Kramer, F.R. (1988) Exponential Amplificatin of Recombinant–RNA Hybridization Probes. Biotechnology 6:1197–1202.

Lomeli, H., Tyagi, S,. Pritchard, C.G., Lizardi, P.M., and Kramer, F.R. (1989) Quantitative Assays Based on the Use of Replicatable Hybridization Probes. Clin. Chem. 35, 1826–1831.

Moore, Melissa J., and Sharp, Phillip A. Site–Specific Modification of Pre–mRNA: The 2'–Hydroxyl Groups at the Splice Sites. Science, 1992, 256:992–997.

Morrissey, D.V., Lombardo, M., Eldredge, J.K., Kearney, K.R., Groody, E.P., and Collins, M.L. (1989) Nucleic Acid Hybridization Assays Employing dA–Tailed Capture Probes: I. Multiple Capture Methods. Anal. Biochem. 81:345–359.

Pritchard, C.G., and Stefano, J.E. (1991) Detection of Viral Nucleic Acids by OB Replicase Amplification. Medical Virology 10(de la Maza, L.M., and Peterson, E.M., eds), pp. 67–80, Plenum Press, New York.

Pritchard, C.G., and Stefano, J.E., Amplified Detection of Viral Nucleic Acid at Subattomole Levels Using QβReplicase. Ann. Biol. Clin. (Paris), 1990; 48:492–497.

Sano, H. and Feix, G. Ribonucleic Acid Ligase Activity of Deoxyribonucleic Acid Ligase From Phage T4 Infected *Escherichia coli*. Biochemistry, 1974, 13/25;5110–5115.

Strobel, S.A., and Cech, T.R., Efficient Ligation of a Highly Structured RNA using T4 DNA Ligase. U.S. Biochem. Corp., 1992, 19/3:89–91.

Syvanen, A.C., Lambsonen, M. and Soderlund, H. (1986) Fast Quantification Nucleic of Acid.Hybrids by Affinity––based Hybrid Collection. Nucleic Acids. Res. 14/12:5037–5048.

Capture Probe 3

```
              10         20         30         40       49
5' Biotin-TACGACTGCT ACCAAGATAA CTTTTCCTTC TAAATGTGTA CAATCTAGC 3'
```

FIG. 2A

Capture Probe 4

```
              10         20         30         40       49
5' Biotin-TACGATGTCT GTTGCTATTA TGTCTACTAT TCTTTCCCCT GCACTGTAC 3'
```

FIG. 2B

Binary Probe 8

```
         10         20         30         40         50         60
5' GGGGACCCCC CCGGAAGGGG GGGACGAGGU GCGGGCACCU CGUACGGGAG UUCGACCGUG 70         80         90
   ACGCUCUAGC AGGCGGCCUU AACUGUAGUA CU 3'
```

FIG. 2C

Binary Probe 9

```
         10         20         30         40         50         60
5' GGUGAAAUUG CUGCCAUUGA GAUCUAGAGC ACGGGCUAGC GCUUUCGCGC UCUCCCAGGU 70         80         90        100        110        120
   GACGCCUCGU GAAGAGGCGC GACCUUCGUG CGUUUCGGUG ACGCACGAGA ACCGCCACGC 130        140        150        160        170        180
   UGCUUCGCAG CGUGGCUCCU UCGCGCAGCC CGCUGCGCGA GGUGACCCCC CGAAGGGGGG

185
   UUCCC 3'
```

FIG. 2D

DIAGNOSTIC ASSAYS AND KITS FOR RNA USING RNA BINARY PROBES AND A PROTEIN THAT IS AN RNA-DIRECTED RNA LIGASE

This is a continuation of application Ser. No. 08/004,993 filed on Jan. 15, 1993 now abandoned.

This invention was made with government support under grant number HL-43521 awarded by the National Institutes of Health. The United States government has certain rights in this invention.

This invention relates to nucleic acid hybridization assays for the detection of RNA. Such assays are broadly applicable to diagnosis of a disease or condition in humans or animals, assays for pathogens in biological samples, and assays for an organism or virus in food, agricultural products or the environment.

BACKGROUND OF THE INVENTION

Nucleic acid hybridization assays of various types are known. There are several assays that utilize a pair of DNA probes and a step of ligating the probes with a DNA ligase, wherein ligation requires that the probes be hybridized adjacent to one another on a target. In this application I use the term "binary probes assay" to refer generally to any assay that includes the step of ligating a pair of probes that are hybridized to a nucleic acid target adjacent to one another. The requirement that the pair of probes be hybridized adjacent to one another on a target means that ligation is "target-dependent." I refer to the pair of probes as "binary reporter probes" or "binary probes."

One binary probe assay is the ligase chain reaction ("LCR") (Barany, 1991). In LCR, a first pair of DNA binary probes is hybridized to one complementary strand of a DNA target and ligated there by a DNA-directed DNA ligase to form a first ligated product, and a second pair of DNA binary probes is hybridized to the first ligated product and similarly ligated to form a second ligated product. By cycling the reaction temperature, steps of melting, annealing probes and ligation are repeated to produce exponentially amplified products, i.e., ligated probes, that are then detected. I sometimes refer to ligated probes as a "reporter molecule" to distinguish from probes per se.

Another binary probe assay for DNA targets utilizes a pair of DNA binary probes, one of which serves to immobilize the target on the surface of a solid and the other of which contains a radioactive atom or fluorescent moiety (Landegren et al., 1988). This assay is reported to apply to RNA targets (using DNA binary probes), but no examples are given (Landegren & Hood, 1991).

A third assay for DNA targets utilizes a pair of DNA binary probes, one of which serves to immobilize the target on the surface of a solid, wherein the reporter molecule is a template that permits exponential amplification by an RNA-directed RNA polymerase such as bacteriophage Qβ replicase (Martinelli et al., 1992). The reporter molecule may be a DNA molecule that is itself a template for Qβ replicase (direct amplification), or it may be template for transcription by bacteriophage T7 RNA polymerase to produce an RNA template for Qβ replicase (indirect amplification).

The assays described above suffer from several drawbacks pertinent here. Most are for DNA targets, for example. That is a drawback, because RNA targets suitable for detection are in most cases much more abundant in samples than their corresponding DNA targets. All of the above assays use DNA binary probes. LCR requires thermal cycling and a thermocycler for amplification, and requires product analysis such as gel electrophoresis. The DNA binary probe assays of Landegren et al., 1988 and Landegren & Hood, 1991 do not include amplification and, therefore, are not sensitive assays. In assays employing exponential amplification by Qβ replicase (Martinelli et al, 1992) the use of DNA probes limits sensitivity: either an additional step of transcription is required, which increases cost, takes additional time, and lowers sensitivity, or a DNA reporter molecule must be amplified directly, which is very inefficient because DNA is not a natural template for Qβ replicase, thereby lowering sensitivity.

There is described in U.S. patent application Ser. No. 08/005,893, now abandoned, for Diagnostic Assays for RNA Using RNA Binary Probes and a Ribozyme Ligase, filed by P. Lizardi, myself, U. Landegren, F. Kramer and J. Szostak on the same day as this application, nucleic acid hybridization assays for the detection of RNA targets using RNA binary probes and a ribozyme ligase, an RNA molecule such as that described in Doudna & Szostak, 1989. Assays utilizing the ribozyme ligases disclosed in that application have several drawbacks. The SunY ribozyme ligase is disclosed to be permissive of incorrectly hybridized probes. The *Tetrahymena ribozyme* ligase requires one probe to have a hybridization length (probe section) of no more than nine nucleotides, which necessitates hybridization and washing conditions that tend to reduce the specificity of the assay. The present invention does not use ribozyme ligases.

It is an object of this invention to overcome the limitations of existing binary probe assays that use DNA binary probes.

It is a further object of this invention to enable use of a pair of RNA probes that both are highly specific for their target.

It is a further object of this invention to enable use of highly specific binary probes that, when ligated, form a reporter molecule that is directly and efficiently amplifiable by incubation with an RNA-directed RNA polymerase.

These and other objects of this invention will be apparent from the description that follows.

SUMMARY OF THE INVENTION

The assays of this invention are nucleic acid hybridization assays for RNA targets using RNA binary probes and a specific and efficient RNA-directed RNA ligase that is a protein.

Preferred embodiments are assays that include exponential amplification at a single temperature for signal generation, most preferably amplification by an RNA-directed RNA polymerase such as Qβ replicase (Lizardi et al., 1988; Lomeli et al., 1989).

Preferred embodiments are sandwich hybridization assays (Syvanen et al., 1986).

Preferred embodiments also use techniques for reducing background, such as, for example, reversible target capture (Morrissey et al., 1989; Hunsaker et al., 1989).

Especially preferred embodiments utilize background reduction techniques disclosed in U.S. patent application Ser. No. 08/006,073, now abandoned, for Sensitive Nucleic Acid Sandwich Hybridization Assays and Kits, filed on the same day as the instant application by myself and U. Landegren, P. Lizardi and F. Kramer (hereinafter Tyagi et al. Ser. No. 08/006.073, now abandoned).

We have discovered certain proteins that function as efficient RNA-directed RNA ligases in the assays of this invention. Our preferred RNA-directed RNA ligase is bacteriophage T4 DNA ligase. It is target-dependent, having a low ligation efficiency in the absence of target; it is believed to be intolerant of mismatched hybrids, especially mismatches at the ligation junction; it accepts probes both having long probe sequences that assure specificity to a target sequence; and it is more than sufficiently efficient, that is, it enables extremely sensitive assays. A protein that is a ligase useful in assays of this invention is one that permits the detection of 100,000 target molecules in the assay of Example 1.

We have developed a simple test to rapidly identify candidate proteins.

This invention also includes diagnostic kits for preselected targets containing a pair of RNA binary probes, a ligase that is a protein, and instructions for performing an assay according to this invention. Additional reagents may be included in preferred kits.

A detailed description of preferred embodiments of this invention, including particularly preferred embodiments, follows in the Detailed Description. Neither the Detailed Description nor the examples are intended to limit the scope of this invention or the appended claims.

BRIEF DESCRIPTION OF THE DRAWINGS

FIGS. 2A, 2B, 2C and 2D (collectively hereafter "FIG. 2") show the sequences of the probes of Example 1 (SEQ. ID. Nos: 1–4)

DETAILED DESCRIPTION

Figure 7:
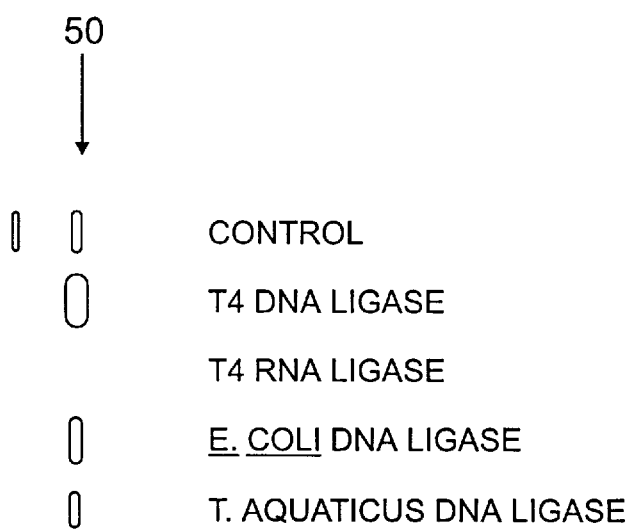
FIG. 7 is an autoradiogram showing the results of a screening test according to Example 2.

We have devised a straightforward screening test to identify proteins that are potentially useful in assays according to this invention. That test is described below in Example 2. It utilizes an RNA target and a pair of RNA binary probes, both of which are highly specific for the target, assuring specificity. Results of one test are shown in FIG. 7, an autoradiogram of the test product. The test includes not only a protein being tested as an RNA-directed RNA ligase (or several of them), but also a control in which no ligase is used. If the autoradiogram shows significantly more amplified product in a reaction containing a particular protein than in a control reaction containing no ligase, as discerned by the naked eye, then that protein is a candidate for further testing to see if it is useful as a ligase in assays of this invention.

FIG. 7 shows that two proteins, T4 DNA ligase and *E. coli* DNA ligase, led to significantly more product than the control without ligase. They are sufficiently efficient for further testing. Neither T4 RNA ligase nor *Thermus aquaticus* DNA ligase showed promise in the screening test, however. Neither is a candidate for further testing. Because T4 DNA ligase visually was more efficient than *E. coli* DNA ligase, we prefer it and have used it in the assays of Example 1.

If a protein appears from the screening test to be a candidate ligase, it can then be used in the assay of Example 1 to determine whether or not it is an "efficient ligase," that is, one useful in assays of this invention. An efficient ligase is defined for purposes of this invention, including the appended claims, as one that permits the detection of 100,000 target molecules in the assay of Example 1. The ability to detect any given quantity of target molecules in the assay of Example 1 is a function of both a protein's target-dependent ligation efficiency and the protein's propensity for target-independent ligation, which tends to increase background. A preferred ligase is one that permits the detection of 1,000 target molecules in the assay of Example 1. A most preferred ligase is one that permits the detection of 100 molecules in the assay of Example 1. T4 DNA is a most preferred ligase. It permits the detection of 100 target molecules in the assay of Example 1. We estimate that in that assay, T4 DNA ligase has a ligation efficiency of ten percent, plus or minus two percent. Of course, the screening test according to Example 2 may be skipped, with the assay of Example 1 being used directly to determine whether or not a particular protein is an efficient ligase.

The assays of this invention are for RNA targets. They require RNA binary probes and a protein that is an efficient RNA-directed RNA ligase. With those restrictions, any appropriate assay protocol can be used. The ligated product, here referred to as an RNA "reporter molecule," may itself be detected, i.e., without being amplified, in assays analogous to known assays using DNA binary probes (Landegren et al., 1988; Landegren and Hood, 1991). Alternately, the RNA binary probes may be designed such that the reporter molecule produced by their ligation is amplifiable, i.e., a template for an RNA-directed RNA polymerase, such as Qβ replicase (see Lizardi et al., 1988; Lomeli et al., 1989; Pritchard and Stefano, 1991; Martinelli et al., 1992, for examples of appropriate RNA molecules).

The assays of this invention may utilize one of the RNA binary reporter probes to immobilize target molecules on a solid surface, analogously to several of the above references that do so for DNA probes.

Preferred assays according to this invention utilize binary probes that both are "highly specific" for their target, by which we mean probes having a probe section of at least 15 nucleotides hybridizable with the target sequence.

Preferred assays according to this invention utilize exponential amplification of RNA reporter molecules by an RNA-directed RNA polymerase, as described above. In addition, preferred embodiments of assays according to this invention utilize techniques for reducing background, such as, for example, reversible target capture (Morrissey et al., 1989; Hunsaker et al., 1989).

The most preferred embodiment of an assay according to this invention utilizes exponential replication of reporter molecules, specifically by Qβ replicase, in conjunction with the background reduction techniques disclosed in Tyagi et al. Ser. No. 08/006,073, now abandoned, which is incorporated herein by reference. The background reduction techniques are the use of a separate capture probe, hybridizable to the target at a site different from the target sequence to which the binary reporter probes hybridize, to form capture probe-target-reporter probes hybrids, immobilization of those hybrids, and release of reporter probes-target hybrids from the capture probes by cleavage, as by ribonuclease H (RNase H). Example 1 discloses our most preferred assay.

Proteins that are RNA-directed RNA ligases are useful also in assays that include a ligase chain reaction as an amplification step, for example, ligase chain reactions in which all of the nucleic acid components are RNAs. If the protein is not thermostable, protein must be added during each LCR cycle.

As stated earlier, this invention also includes kits for performing assays according to this invention. A preferred kit may contain some or all of the following items:

1. 5M guanidine thiocyanatic (GuSCN) buffer for the lysis of cells in clinical samples;
2. A mixture containing RNA binary reporter probes, preferably highly specific binary probes, for a preselected RNA target and, preferably, DNA capture probes;
3. A solid, such as a dipstick, reaction tube or paramagnetic particles, with streptavidin covalently bound thereto;
4. A magnetic separation device;
5. Nucleotides;
6. An efficient ligate useful in this invention, preferably T4 DNA ligase;
7. RNase H and Qβ replicase;
8. Buffers for ligation and amplification;
9. Reagents for detecting the amplified reporters, such as radioactive alpha-$P^{32}$-cytidine triphosphate or propidium iodide;
10. Instructions for performing an assay according to this invention.

A bare kit may contain only items 2, 6 and 10. A more complete kit will also contain at least items 1, 3 and 7. A kit containing at least items 1–2 and 5–10, where the solid is a dipstick or reaction tube, is particularly useful for assays to be performed outside a well-equipped laboratory.

EXAMPLES

Figure 1:
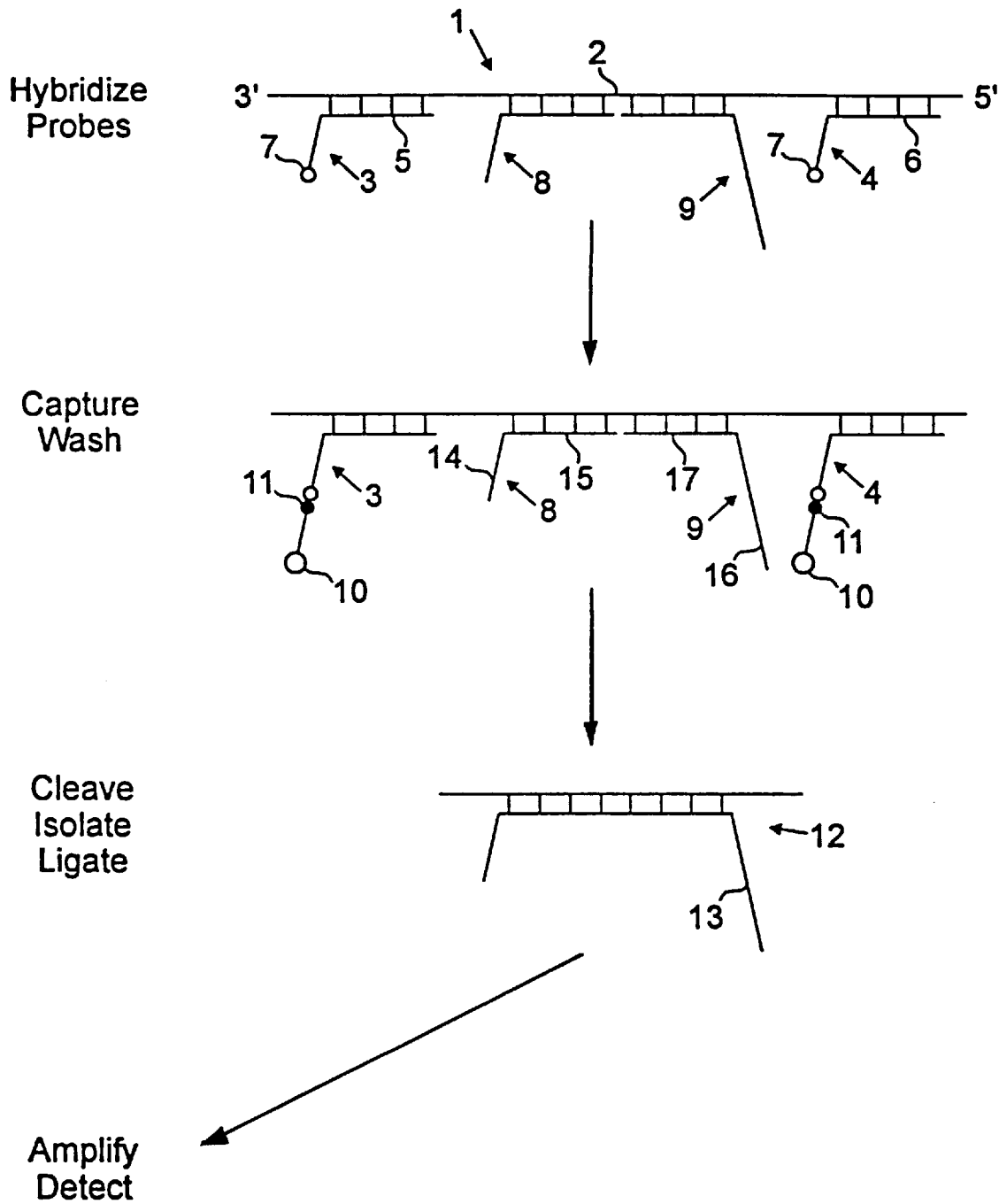
FIG. 1 depicts the assay of Example 1.

Example 1
RNA Target, RNA Binary Probes, DNA Capture Probes, Ribonuclease H Cleavage and T4 DNA Ligase This embodiment, which employs T4 DNA ligase, has led to extremely sensitive assay depicted generally in FIG. 1 for the detection of an RNA target, illustrated here by human immunodeficiency virus ("HIV") RNA. The target sequence 2 of target 1 is located in the integrase region of HIV RNA. The assay begins by dissolving the sample in 5M guanidine thiocyanate (GuSCN). A mixture of four different nucleic acid probes is then added to the sample. These probes hybridize to the HIV RNA, as shown in FIG. 1. Two of the probes are capture probes 3, 4 (SEQ. ID. Nos: 1–2) made of DNA. Each capture probe has a hybridization sequence 5 or 6 at its 3' end that is complementary to the target 1. Capture probes 3, 4 (SEQ. ID. Nos: 1–2) also have a biotin moiety 7 at their 5' ends. The other two probes 8, 9 (SEQ. ID. Nos: 3–4) are highly specific binary reporter probes made of RNA. After hybridization, the hybrids are captured on the surface of paramagnetic particles 10 coated with streptavidin 11, which binds tightly to the biotin moiety 7 of the capture probes. The paramagnetic particles 10 are then washed extensively to remove unhybridized binary probes. Stringent washing with 2M GuSCN rather than a more dilute solution, e.g., 1M GuSCN, can be used because the binary probes both are highly specific. RNase H is then added to cleave the target RNA in the region where it is hybridized to the capture probes. Cleavage of the target RNA frees the binary probe-starget hybrids 12 (shown in FIG. 1 after ligation) from the capture probes.

The cleavage release step is quantitative and specific. The binary probes that nonspecifically adhere to the DNA capture probes or to the surface of the paramagnetic particles (i.e., sources of the background signal) are not released by this cleavage. The paramagnetic particles 10 are discarded.

In the supernatant, pairs of binary probes that are correctly hybridized adjacent to one another on their targets are ligated to each other in a target-dependent manner using a ligase that is a protein, in this case T4 DNA ligase. The ligated probes 13 are then amplified by incubation with Qβ replicase. The amplified signal is strictly dependent on the presence of the target, and the level of the signal as a function of time can be used to determine quantitatively the number of molecules of HIV RNA in the initial sample.

A. Synthesis of the Probes

The capture probes used in this example (FIG. 2) have three functional parts. A head of 40–50 nucleotides which hybridize to the preselected target, a spacer of about 4 nucleotides, and a tail that binds tightly to the solid surface. We chose the tail to be a biotin moiety and covalently linked it to the 5' end of each capture probe. The biotin moiety can be attached anywhere in the capture probe, including at the 3' end and internally. The tail can be made up of some other affinity reagent, such as a homopolynucleotide.

FIG. 1 shows the manner in which capture probes 3, 4 (SEQ. ID. Nos: 1–2) bind to target 1. Two different capture probes were used, rather than one, in order to increase the efficiency of capture and increase the stringency of release of the binary probe-target complexes. The two capture probes 3, 4 (SEQ. ID. Nos: 1–2) bind to target 1 on either side of the target sequence 2 to which the binary probes bind. Hybridization sequence 5 of capture probe 3 (SEQ. ID. No: 1) is complementary to region 4415-4458 of HIV genomic RNA, and hybridization sequence 6 of capture probe 4 (SEQ. ID. No: 2) is complementary to region 4808-4852 of HIV genomic RNA. FIG. 2 shows the sequences of the two capture probes 3, 4 (SEQ. ID. Nos: 1–2) used in this example. Underlines indicate hybridization sequences 5, 6 that are complementary to the target RNA. Both of the capture probes were prepared on a DNA synthesizer.

The desired reporter molecule of this particular embodiment requires the ligation of two binary probes, as shown in FIG. 1. The use of binary probes is a preferred embodiment. FIG. 1 illustrates the design of highly specific binary reporter probes 8, 9 (SEQ. ID. Nos: 3–4). The 5' end 14 of probe 8 (SEQ. ID. No: 2) consists of the first sixty-nine nucleotides of the replicatable probe for HIV used in our previous studies (Lomeli et al., 1989). The next twenty-three nucleotides are probe sequence 15, which is complementary to region 4596-4618 of HIV genomic RNA. The 5' end of probe 9 (SEQ. ID. No: 4) consists of 19-nucleotide probe sequence 17, which is complementary to region 4577-4595 of HIV genomic RNA. The remainder 16 of probe 9 (SEQ. ID. No: 4) corresponds to nucleotides 95–280 of the replicatable probe for HIV used in our previous studies (Lomeli et al., 1989). FIG. 2 shows the sequences of binary probes 8, 9 (SEQ. ID. Nos: 3–4). Underlines indicate hybridization sequences 15, 17 that are complementary to the target sequence. Hybridization sequences 15, 17 both being at least fifteen nucleotides in length, probes 8, 9 (SEQ. ID. Nos: 3–4) are "highly specific" according to this invention. Neither of these molecules is a good replicator when incubated with Qβ replicase, but if they are ligated to each other, they form an exponentially replicatable reporter molecule.

Figure 3:
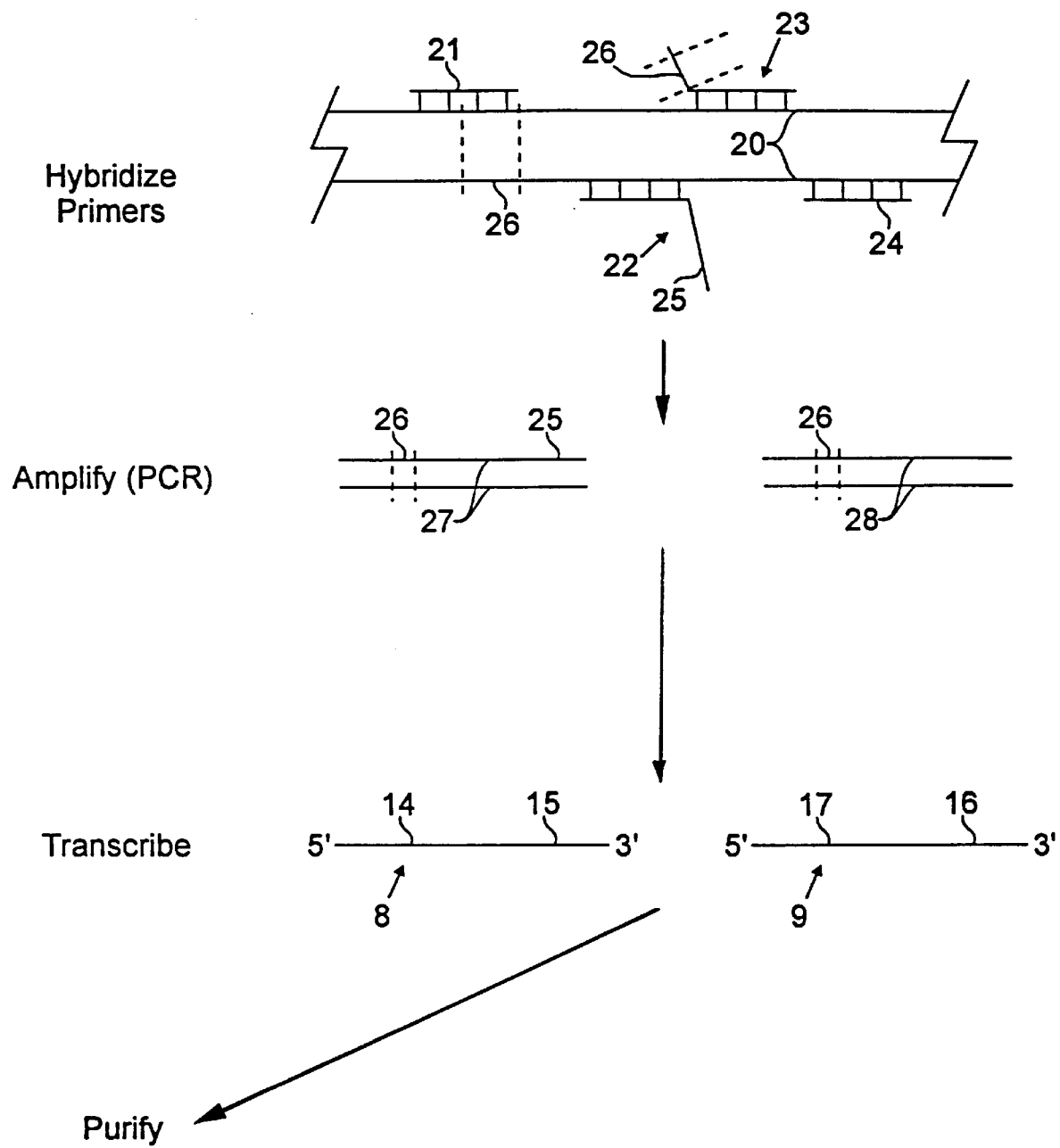
FIG. 3 depicts the preparation of binary probes of Example 1. (SEQ. ID. Nos: 1–4)

Binary probes 8, 9 (SEQ. ID. Nos: 3–4) were prepared by transcription from DNA templates generated in a polymerase chain reaction (PCR) shown in FIG. 3. The plasmid 20 described in Lomeli et al., 1989 at page 1827, which we call plasmid pT7MDVHIV20, was used as the source of MDV sequences in the PCR reactions. The relevant section of the plasmid is shown in FIG. 3. It is, of course, double-stranded. Four PCR primers 21, 22, 23 and 24 were designed in such a way that they contributed additional sequences to the PCR products 27, 28 that were not present in plasmid 20, but which were required. PCR product 27 is generated from primers 21, 22. PCR product 28 is generated from primers 23, 24. Primer 22 provided the terminal twenty-three nucleotides 25 in the template for probe 8 (SEQ. ID. No: 3). Primer 23 provided T7 promoter 26 at the 5' end of the template for probe 9 (SEQ. ID. No: 4). (Plasmid 20 provided a T7 promoter in the region of primer 21.) Probe 8 (SEQ. ID. No: 3) was transcribed in the usual manner from its PCR template, but the synthesis of probe 9 (SEQ. ID. No: 4) required a modification in the conditions of transcription by T7 RNA polymerase. The donor of the phosphate group in a ligation reaction, in this case probe 9 (SEQ. ID. No: 4), must contain a single phosphate at its 5' end. RNA molecules prepared by transcription usually have a triphosphate at their 5' ends. In order to synthesize probe 9 (SEQ. ID. No: 4) with a single phosphate group at its 5' end, a ten-fold excess of guanosine 5'-monophosphate over the nucleoside 5'-triphosphates was included in the transcription reaction. This lead to the incorporation of guanosine 5'-monophosphate at the first position of the probe 9 (SEQ. ID. No: 4). As a result, the copies of probe 9 (SEQ. ID. No: 4) possessed the required monophosphate at their 5' ends. After transcription, each of the binary probe RNAs 8, 9 (SEQ. ID. Nos: 3–4) was purified by preparative polyacrylamide gel electrophoresis. The RNA was eluted directly from the gel slice into a 2M guanidine thiocyanate (GuSCN) solution.

We have discovered since this example was performed that probe 9 (SEQ. ID. No: 4) can be improved by using a twenty-fold excess of guanosine 5'-monophosphate rather than the ten-fold excess reported above. Efficiency of ligation triples, from ten percent to thirty percent, when the greater excess is used, with T4 DNA ligase as the RNA-directed RNA ligase.

B. Hybridization, Capture, Washing, and Release

The assay of this example has been performed on samples containing known amounts of HIV RNA molecules. This assay is used to ascertain whether or not a particular protein is an "efficient ligase" useful in assays according to this invention. It will be described with reference to a test of T4 DNA ligase. An RNA corresponding to the mRNA of the integrase gene of HIV was used as a model target. This RNA was prepared by transcription from linearized plasmid pGEM-integrase, that was prepared in our laboratory. Eight tubes containing differing amounts, for example, 10000000, 1000000, 100000, 10000, 1000, 100, 10, and 0 molecules, of integrase RNA in 50 microliters of 2M GuSCN were prepared by serial dilution. A 2M GUSCN solution (50 microliters) containing $10^{13}$ molecules of each of the capture probes and $2 \times 10^{10}$ molecules of each of the binary probes was added to each tube. Hybridization was carried out by incubation at 37 degrees centigrade for one hour. A 30-microliter suspension of paramagnetic particles coated with streptavidin (Promega) was then added to this hybridization mixture. The probes-target hybrids were captured on the surface of the paramagnetic particles by a 10-minute incubation at 37 degrees centigrade. The particles were washed with 2M GuSCN four times, with 300 mM KCl three times, and finally with 1×ligase buffer (66 mM Tris-HCl, pH 7.5, 5 mM $MgCl_2$, 1 mM DTT, 1 mM ATP) two times. After washing, one unit of *E. coli* RNase H (Pharmacia) dissolved in 50 microliters of 1×ligase buffer was added. The binary probes-target hybrids were released from the surface of the paramagnetic particles by a 10-minute incubation at 37 degrees centigrade. The tubes containing the mixture were placed in the magnetic field provided by a magnetic separation device to draw the paramagnetic particles to the walls of the test tubes. The supernatant was then separated from the paramagnetic particles by aspiration and placed into a fresh tube.

The probe-target hybrids were then incubated with the candidate protein, T4 DNA ligase, in order to ligate the binary probes that were correctly hybridized to targets. Ligation was carried out in 40 microliters of the supernatant by the addition of 40 units of T4 DNA ligase and incubation at 37 degrees centigrade, which was appropriate for this protein, for one hour.

The assay of this example has also been performed with T4 DNA ligase on samples containing known amounts of HIV-infected cells. In order to demonstrate the specificity and sensitivity of this assay with clinical samples, human peripheral lymphocytes were infected with HIV. These infected cells were serially diluted with uninfected human peripheral lymhocytes. Eight tubes were prepared, containing differing amounts, for example, 600000, 60000, 6000, 600, 60, 6, 0, and 0 infected cells. Each of these tubes had the same total number of cells, for example, 600000. The tubes were centrifuged and the supernatant was removed. 240 microliters of 5M GuSCN was added to each tube. The tubes were then incubated for 2 hours at 37° C. in order to lyse the cells. After lysis, 40 microliters from each tube were assayed. A 60 microliter solution containing all four probes was added to the lysate. The addition of this solution reduced the GuSCN concentration in the lysate to 2M. Hybridization and all subsequent reactions were carried out the same as described in the previous paragraph.

C. Amplification

The reporter molecules, comprising ligated binary probes, were then amplified by incubation with Qβ replicase. It is not necessary to melt apart the reporter molecule-target hybrids prior to amplification. A mixture containing all of the components of the replication reaction was added to each of the eight tubes. The final reaction mixture (120 microliters) was 45 mM Tris-HCl (pH 8), 10 mM $MgCl_2$, 400 micromolar ATP, 400 micromolar GTP, 400 micromolar UTP, 400 micromolar alpha-$P^{32}$-CTP, and contained 50 micrograms per milliliter Qβ replicase. Each reaction was incubated at 37 degrees centigrade, and 4-microliter samples were withdrawn from each reaction every minute in the interval between 10 to 31 minutes of incubation. Each sample was mixed with a 45-microliter stop solution (120 mM NaCl, 20 mM EDTA, and 3 microgram per ml protein-ase K). This solution stops replication by sequestering the required magnesium ions. The stop solutions were arranged in titerplates before addition of the samples. The RNA in each stopped reaction was separated from the unincorporated nucleoside triphosphates by precipitating the RNA in an acidic solution (360 mM phosphoric acid, 20 mM sodium pyrophosphate, and 2 mM EDTA), trapping the precipitate on a blotting membrane (Zeta Probe, Biorad), and then washing the membrane with the acidic solution. The RNA on the blots was visualized by autoradiography.

D. Results

Figure 4:
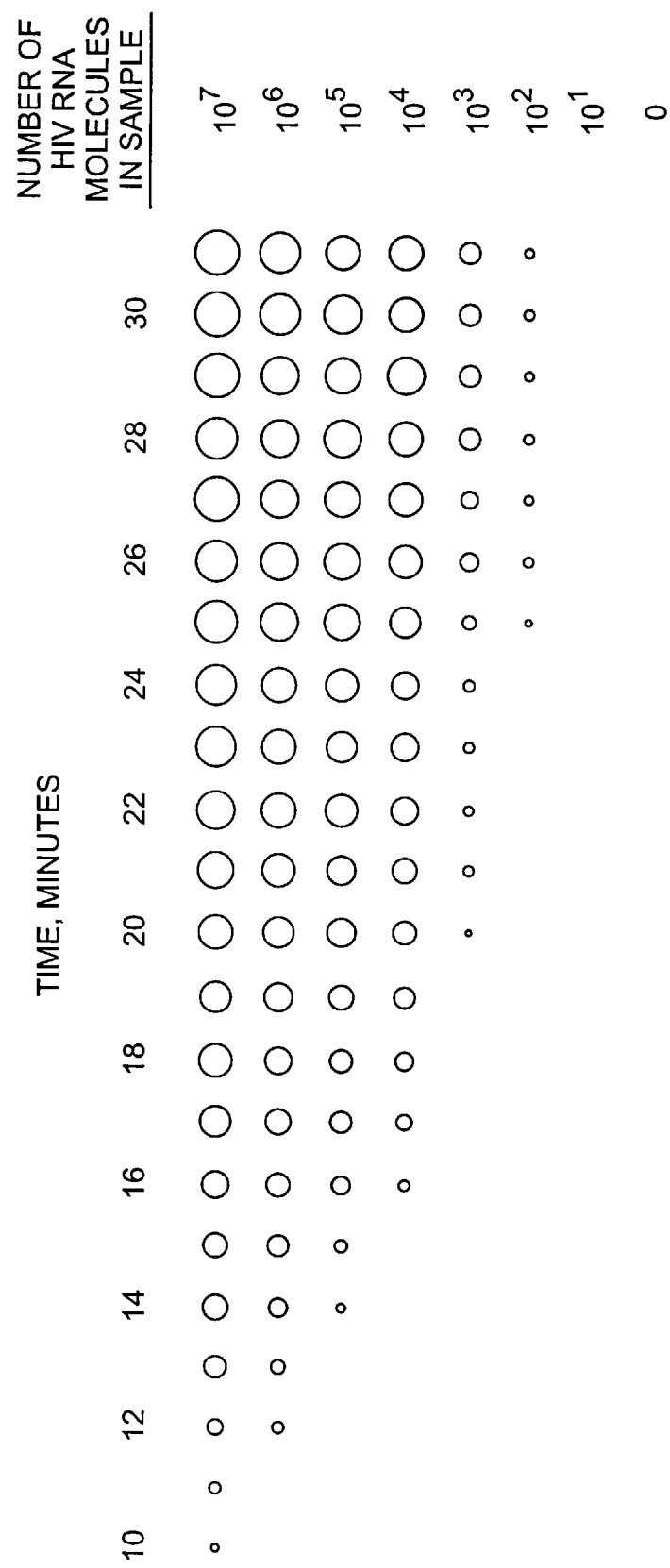
FIG. 4 shows results of a test assay according to Example 1 for a candidate ligase, T4 DNA ligase.

The results demonstrate that T4 DNA ligase is an "efficient ligase" for use in assays according to this invention. FIG. 4 shows a typical result of the assay described above for a dilution series of molecules of HIV integrase RNA. FIG. 4 is an autoradiogram. Each row depicts the signal from a given sample over time, as indicated. The intensity of each dot in FIG. 4 is proportional to the amount of RNA that was present in the tube at the time the sample was withdrawn. The time at which RNA can first be seen in the autoradiogram depended upon the number of targets that were present. The greater the number of targets, the earlier the signal appeared. There is a delay of at least about two-minutes for every 10-fold decrease in the number of targets. As few as a 100 targets molecules gave rise to a clear signal. Ten target molecules, or no target molecules, did not produce a signal, even after an additional eight minutes of incubation (not shown). One hundred molecules of HIV RNA target were clearly detectable; and anything less gave no signal at all.

As stated, the minimum number of targets that could be detected in this assay using T4 DNA ligase was a hundred molecules. We have determined by other experiments that the efficiency of ligation was ten percent plus or minus two percent. Based on our experience and on FIG. 7, we estimate that ligation efficiency of E. coli DNA ligase in this assay to be about one percent, but we have not determined its efficiency by other experiments. The improvement in synthesis of probe 9 reported above, which triples ligation efficiency, will improve the sensitivity of this assay even more, but to determine whether or not a candidate ligase is an "efficient ligase" useful in assays according to this invention, the probes actually used in this example are used.

Figure 5:
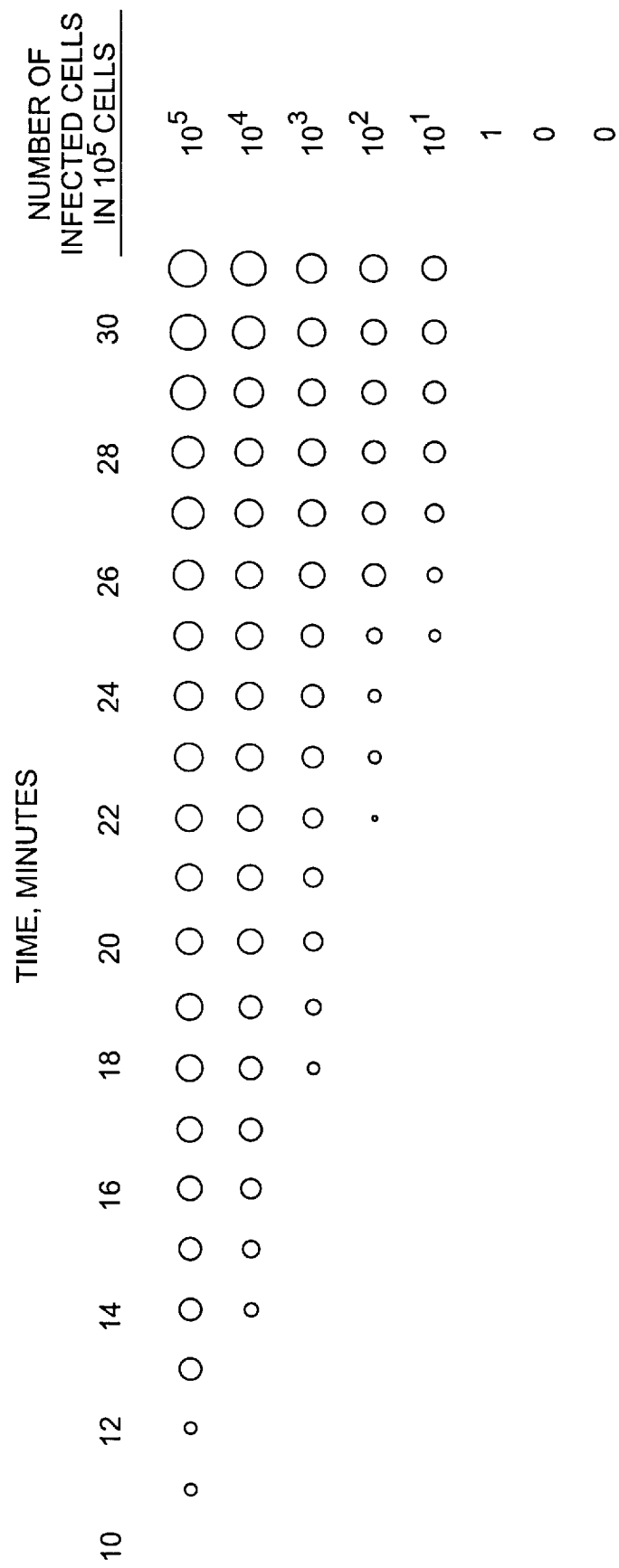
FIG. 5 shows the results of an assay of infected cells according to Example 1 using T4 DNA ligase.
Figure 6:
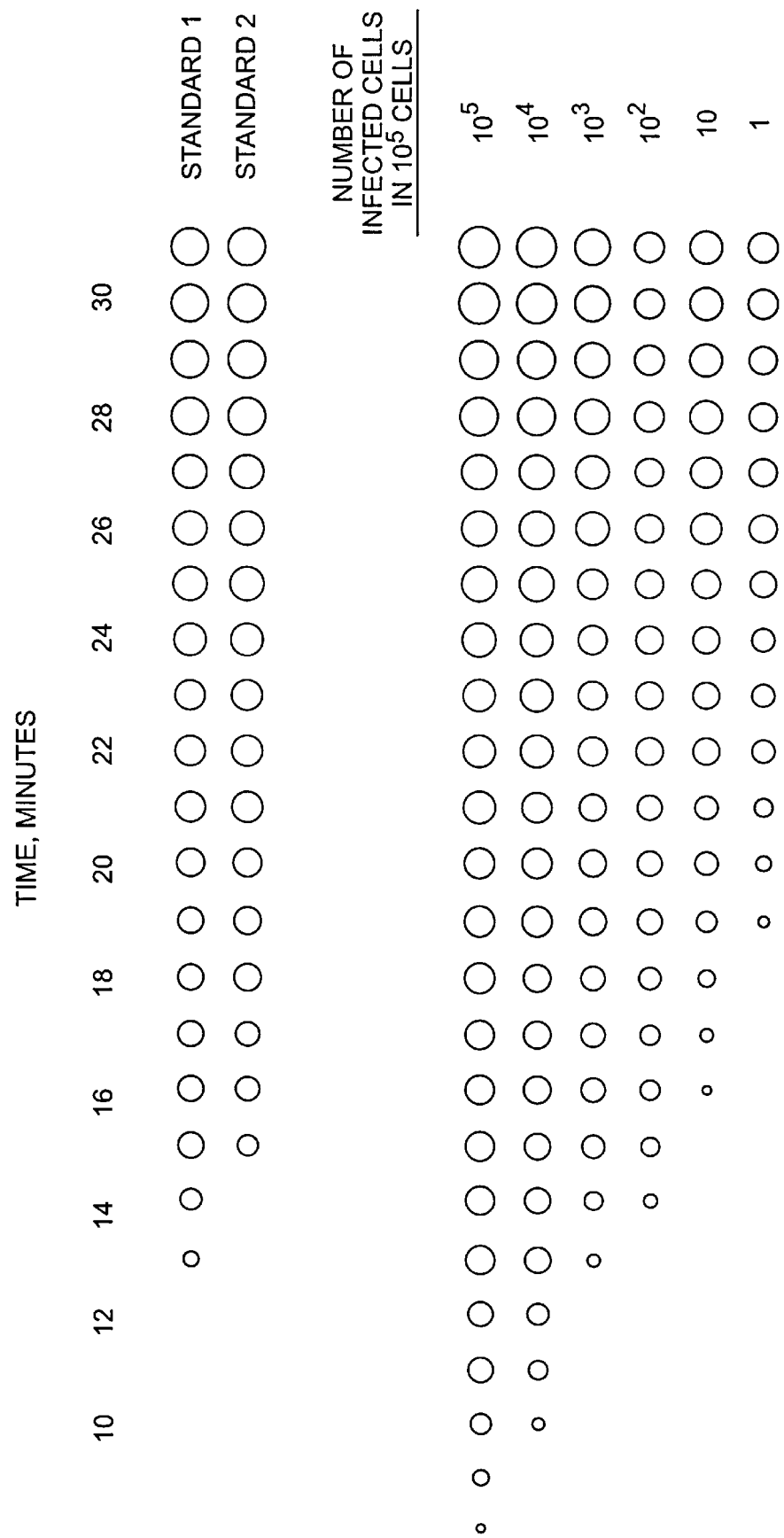
FIG. 6 shows the results of another assay according to Example 1 for known amounts of infected cells.

FIGS. 5 and 6 depict the results of assays according to this example with T4 DNA ligase on samples containing HIV-infected human peripheral lymphocytes. FIGS. 5 and 6 are autoradiograms as described in connection with FIG. 4. The results of the two experiments, when considered together, show that one infected cell can be detected in a sample containing 100,000 uninfected cells, and that no signal is seen in samples that contain no infected cells. In both experiments each sample contained a total of 100,000 cells. In the first experiment (FIG. 5), the results show a clear relationship between the number of infected cells in a sample and the time of appearance of the signal. The greater the number of infected cells, the earlier the signal appeared. Thus, the assay is quantitative as well as qualitative. The two controls, each of which contained 100,000 uninfected cells (and no infected cells), produced no signal. However, the tube that contained one infected cell also did not give a signal. We hypothesized that, after lysis, the sample was not mixed completely. The lysed samples are extremely viscous (due to the presence of cellular DNA), and since there were only about six infected cells in the 240 microliter volume of the lysate, the probability of not sampling any HIV RNA in the 40 microliter sample withdrawn from the sample for the assay was high. In order to eliminate such a possibility, the samples were frozen and thawed and then exhaustively mixed, prior to using them in the next experiment. The assay was repeated with these well-mixed samples. The results, shown as the bottom six samples in FIG. 6, demonstrate that our hypothesis was correct and that, after proper mixing, the tube containing the nucleic acid from about one infected cell gave a strong signal with an appropriate delay time.

Another objective of the second experiment was to estimate the number of molecules of HIV RNA in each infected cell. We prepared two standards for this purpose. Standard 1, the first standard tube, contained 1,000,000 HIV integrase mRNA transcripts. Standard 2, the second lysate from 100,000 uninfected cells and 1,000,000 molecules of HIV integrase mRNA transcripts. The results of the experiment, shown as the top two samples in FIG. 6, show that the presence of lysate from the uninfected cells has only a slight quenching effect. From the signal obtained from this internal standard, we were able to estimate that each infected cell contained about 3,000 HIV target molecules.

A note of caution is in order. Our laboratory is used for research on replicatable RNA molecules, which have a tendency to become airborne contaminants. In a test of the above assay, we obtained an aberrant signal in one of the tubes. Electrophoretic analysis of the amplified RNA revealed that it was not the reporter. Qβ replicase will amplify a number of RNAs, and our sample had become contaminated.

Example 2

Selection of an Appropriate Ligase

We have developed an extremely sensitive screening procedure for identifying RNA-directed RNA ligase activities of candidate proteins. By this procedure we have identified at least two proteins that can catalyze RNA-directed RNA ligation. Following is a description of the screening procedure.

Ten billion HIV integrase mRNA molecules were hybridized to a large excess of RNA binary probes and DNA capture probes. The reporter probes-hybrids were then captured, washed and released from the capture probes by incubation with RNase H, in the manner described in Example 1. The released material was divided into five aliquots. A candidate protein was added to four of the each aliquots so that the five aliquots contained; no ligase, T4 DNA ligase, T4 RNA ligase, E. coli DNA ligase, and a DNA ligase isolated from the thermophilic organism, Thermus aquaticus. The reaction mixture for the last two ligases also contained 1 mM NAD, which is a required cofactor. The first four reactions were incubated at 37 degrees centigrade, while the last reaction was incubated at 55 degrees centigrade. All the reactions were incubated for one hour. After ligation, the ligated binary probes were amplified by incubation with Qβ replicase for 15 minutes at 37 degrees centigrade. The products were fractionated by electrophoresis on a polyacrylamide gel.

FIG. 7 is the resulting autoradiogram. It shows the gel fraction 50 corresponding to amplified reporter molecule for each aliquot. T4 DNA ligase was sufficiently efficient to be a candidate for use in this invention. It catalyzed the synthesis of the largest amount of ligated product. E. coli DNA ligase also worked well and was judged to be a candidate. The DNA ligase from T. aquaticus gave a result not visually distinguishable from the control containing no ligase. It did not work, at least not sufficiently efficiently to be a candidate for use in this invention.

To be considered as a candidate ligase for use in this invention, as stated above, a protein must give results, i.e., amplified product 50, that can be readily seen by the naked eye to be larger than the product (background) from the control with no ligase. On the basis of this extremely sensitive procedure, we selected T4 DNA ligase as a candidate for use in our assays. It was subjected to the assay of Example 1 and found to be an "efficient Ligase" useful in assays according to this invention. It was in fact found to be a most preferred ligase that permitted the detection of 100 molecules. This ligase was also found to be particularly "efficient" for the ligation of DNA binary probes that are hybridized to an RNA target.

References

Barany, F. (1991) Genetic Disease Detection and DNA Amplification Using Cloned Thermostable Ligase. Proc. Natl. Acad. Sci. U.S.A. 88, 189–193.

Doudna, J. A. and Szostak, J. W. (1989) RNA-catalyzed Synthesis of Complementary-Strand RNA. Nature 339, 519–522.

Hunsaker, W. R., Badri, H., Lombardo, M. and Collins, M. L. (1989) Nucleic Acid Hybridization Assays Employing dA-Tailed Capture Probes. II. Advanced Multiple Capture Methods. Anal. Biochem. 181, 360–370.

Landegren, U., Kaiser, R., Sanders, J., and Hood, L. (1988) A Ligase-mediated Gene Detection Technique. Science 241, 1077–1080.

Landegren, U., and Hood, L. (1991) Method of Detecting a Nucleotide Change in NucleicAcids. U.S. Pat. No. 4,988,617.

Lizardi, P., Guerra, C. E., Lomeli, H., Tussie-Luna, I., and Kramer, F. R. (1988) Exponential Amplification of Recombinant-RNA Hybridization Probes. Biotechnology 6, 1197–1202.

Lomeli, H., Tyagi, S., Pritchard, C. G., Lizardi, P. M., and Kramer, F. R. (1989) Quantitative Assays Based on the Use of Replicatable Hybridization Probes. Clin. Chem. 35, 1826–1831.

Martinelli, R. M., Donahue, J. J., and Unger, J. T. (1992) Amplification of Midivariant DNA Templates. European Patent Application Publication No. 0 431 704 A1.

Morrissey, D. V., Lombardo, M., Eldredge, J. K., Kearney, K. R., Goody, E. P., and Collins, M. L. (1989) Nucleic Acid Hybridization Assays Employing dA-Tailed Capture Probes: I. Multiple Capture Methods. Anal. Biochem. 81, 345–359.

Pritchard, C. G., and Stefano, J. E. (1991) Detection of Viral Nucleic Acids by Qβ Replicase Amplification. Medical Virology 10 (de la Maza, L. M., and Peterson, E. M., eds), pp 67–80, Plenum Press, New York.

Syvanen, A. C., Lambsonen, M. and Soderlund, H. (1986) Fast Quantification of Nucleic Acid Hybrids by Affinity-based Hybrid Collection. Nucleic Acids Res. 14, 5037–5048.

---

We claim:

1. A nucleic acid hybridization assay to determine the presence in a sample of an RNA target containing a preselected target sequence, comprising the steps of:
   a. incubating the sample with RNA binary probes complementary to adjacent portions of the preselected target sequence to form an RNA binary probes-target sequence hybrid wherein said RNA binary probes are hybridized adjacent to one another on the target sequence,
   b. adding to said RNA binary probes-target sequence hybrid a protein that is an efficient RNA-directed RNA ligase,
   c. ligating said RNA binary probes of said RNA binary probes-target sequence hybrid in a target-dependent manner with said protein to form an RNA reporter molecule, and
   d. detecting said RNA reporter molecule as an indication of the presence in the sample of the RNA target containing the preselected target sequence.

2. The assay according to claim 1, wherein said protein added in step (b) is a ligase which, when used in the test assay reported in Example 1 hereof, with the capture probes, binary probes, RNA model target and assay conditions there reported, the step of detecting is positive for said RNA reporter molecule when as few as 1000 RNA model target molecules are initially present in the sample.

3. The assay according to claim 1, wherein said protein added in step (b) is a ligase which, when used in the test assay reported in Example 1 hereof, with the capture probes, binary probes, RNA model target and assay conditions there reported, the step of detecting is positive for said RNA reporter molecule when as few as 100 RNA model target molecules are initially present in the sample.

4. The assay according to claim 1, wherein said protein is T4 DNA ligase.

5. The assay according to claim 1, wherein said protein is *Escherichia coli* DNA ligase.

6. The assay according to claim 1, wherein one of said binary probes serves to immobilize the target on the surface of a solid and the other of said binary probes is detectable.

7. The assay according to claim 1, wherein said binary probes are highly specific for said target sequence.

8. A nucleic acid hybridization binary probe assay to determine the presence in a sample of an RNA target containing a preselected target sequence, comprising the steps of:
   a. incubating the sample with RNA binary probes comprising a first probe and a second probe complementary to adjacent portions of the preselected target sequence to form an RNA binary probes-target sequence hybrid, wherein said RNA binary probes are hybridized adjacent one another on the target sequence, and wherein one of said first or second binary probes serves to immobilize the RNA target on a solid surface,
   b. washing the immobilized RNA binary probes-target sequence hybrid,
   c. adding to the RNA binary probes-target sequence hybrid a protein that is an efficient RNA-directed RNA ligase,
   d. ligating said RNA binary probes of said RNA binary probes-target sequence hybrid in a target-dependent manner with said protein to form an amplifiable RNA reporter molecule,
   e. incubating said RNA reporter molecule with an RNA-directed RNA polymerase to form an amplified product, and f. detecting the presence of said amplified product as an indication of the presence in the sample of said RNA target containing the preselected target sequence.

9. The assay according to claim 8, wherein said ligase added in step (c) is a ligase which, when used in the test assay reported in Example 1 hereof, with the capture probes, binary probes, RNA model target and assay conditions there reported, the step of detecting is positive for said RNA reporter molecule when as few as 1000 RNA model target molecules are initially present in the sample.

10. The assay according to claim 8, wherein said protein is T4 DNA ligase.

11. The assay according to claim 8, wherein said binary probes are highly specific for said target sequence.

12. The assay according to claim 11, wherein said RNA-directed RNA polymerase is Qβ replicase.

13. The assay according to claim 11, including a step of reversible target capture between steps (b) and (c).

14. The assay according to claim 11, wherein said protein is T4 DNA ligase.

15. A kit of reagents for performing a binary probe hybridization assay for the detection in a sample of an RNA target containing a preselected target sequence comprising:
  a. RNA binary probes complementary to said target sequence, said RNA binary probes when ligated form replicatable RNA reporter molecules,
  b. a protein that is an efficient RNA-directed RNA ligase, and
  c. instructions for performing the assay.

16. The kit according to claim 15, wherein said protein is T4 DNA ligase.

17. The kit according to claim 15, wherein said protein is *Escherichia coli* DNA ligase.

18. The kit according to claim 15, wherein said protein is a ligase which, when used in the test assay reported in Example 1 hereof, with the capture probes, binary probes, RNA model target and assay conditions there reported, the step of detecting is positive for said RNA reporter molecule when as few as 1000 RNA model target molecules are initially present in the sample.

19. The kit according to claim 15, further comprising an RNA-directed RNA polymerase which exponentially amplifies a ligated product of said RNA binary probes.

20. In a binary probe hybridization assay for the detection of an RNA target containing a preselected target sequence in a sample, utilizing binary probes, said assay including annealing the binary probes to the preselected target sequence, joining the probes and detecting the joined probes as an indication of the presence of the RNA target in the sample, the improvement comprising using RNA binary probes and joining said RNA binary probes by target-dependent ligation by a protein that is an efficient RNA-directed RNA ligase to form an RNA reporter molecule.

21. The assay according to claim 20, wherein said protein is T4 DNA ligase.

22. The assay according to claim 20, wherein said RNA binary probes are highly specific for said target sequence.

23. The assay according to claim 22, wherein said protein is a ligase which, when used in the test assay reported in Example 1 hereof, with the capture probes, binary probes, RNA model target and assay conditions there reported, the step of detecting is positive for said RNA reporter molecule when as few as 1000 RNA model target molecules are initially present in the sample.

24. The assay according to claim 22, wherein said protein is T4 DNA ligase.

25. In an assay for the detection of an RNA target containing a preselected target sequence in a sample that includes a ligase chain reaction as an amplification step utilizing binary probes, said assay including annealing the probes to the RNA target, ligating the probes, amplifying the ligated probes using a ligase chain reaction and detecting a product of the ligase chain reaction as an indication of the presence of the RNA target in the sample, the improvement comprising using RNA binary probes and ligating and amplifying said RNA binary probes by target-dependent ligation utilizing a protein that is an efficient RNA-directed RNA ligase.

26. The assay according to claim 25, wherein the protein is T4 DNA ligase.

27. The kit according to claim 15, wherein said protein is a ligase which, when used in the test assay of Example 1 hereof, with the capture probes, binary probes, RNA model target and assay conditions there reported, the step of detecting is positive for said RNA reporter molecule when as few as 100 RNA model target molecules are initially present in the sample.

28. The assay according to claim 22, wherein said protein is a ligase which, when used in the test assay reported in Example 1 hereof with the capture probes, binary probes, RNA model target and assay conditions there reported, the step of detecting is positive for said RNA reporter molecule when as few as 100 RNA model targets containing a preselected target sequence are initially present in the sample.

29. The assay according to claim 1, wherein during step (c) said protein ligates, in a target-dependent manner, at least about ten percent of said RNA binary probes in said RNA binary probes-target sequence hybrids formed in step (a) in one hour at 37° C.

30. The assay according to claim 8, wherein during step (d) said protein ligates, in a target-dependent manner, at least about ten percent of said RNA binary probes in said RNA binary probes-target sequence hybrids formed in step (a) in one hour at 37° C.

31. The kit according to claim 15 wherein said protein ligates, in a target-dependent manner, at least about ten percent of said RNA binary probes hybridized to the preselected target sequence in one hour at 37° C.

32. An assay according to claim 1, further comprising the step of amplifying said RNA reporter molecule after step (c) and before step (d).

33. An assay according to claim 32, wherein said amplification step comprises a ligase chain reaction.

34. An assay according to claim 33, wherein said ligase chain reaction is performed with a protein which is an efficient RNA-directed RNA ligase.

35. The assay according to claim 32, wherein said reporter molecule is a template for an RNA-directed RNA polymerase, and the step of amplifying comprises incubating said reporter molecule with an RNA-directed RNA polymerase.

36. The assay according to claim 35, further comprising a step of reversible target capture after step (a) and before step (b).

37. The assay according to claim 35, wherein said binary probes are highly specific for said target sequence.

38. An assay according to claim 35, wherein said RNA-directed RNA polymerase is Qβ replicase.

39. The kit according to claim 15 further comprising an RNA model target.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 49 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( v i ) ORIGINAL SOURCE:
      ( A ) ORGANISM: Human immunodeficiency virus type 1

( x i ) SEQUENCE DESCRIPTION: SEQ ID NO:1:

TACGACTGCT ACCAAGATAA CTTTTCCTTC TAAATGTGTA CAATCTAGC 49

( 2 ) INFORMATION FOR SEQ ID NO:2:

( i ) SEQUENCE CHARACTERISTICS:
      ( A ) LENGTH: 49 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( v i ) ORIGINAL SOURCE:
      ( A ) ORGANISM: Human immunodeficiency virus type 1

( x i ) SEQUENCE DESCRIPTION: SEQ ID NO:2:

TACGATGTCT GTTGCTATTA TGTCTACTAT TCTTTCCCCT GCACTGTAC 49

( 2 ) INFORMATION FOR SEQ ID NO:3:

( i ) SEQUENCE CHARACTERISTICS:
      ( A ) LENGTH: 92 base pairs
      ( B ) TYPE: nucleic acid
      ( C ) STRANDEDNESS: single
      ( D ) TOPOLOGY: linear ( i i ) MOLECULE TYPE: RNA (genomic)

(iii) HYPOTHETICAL: NO (vi) ORIGINAL SOURCE:
    (A) ORGANISM: Human immunodeficiency virus type 1

(xi) SEQUENCE DESCRIPTION: SEQ ID NO:3:

GGGGACCCCC CCGGAAGGGG GGGACGAGGU GCGGGCACCU CGUACGGGAG UUCGACCGUG    60

ACGCUCUAGC AGGCGGCCUU AACUGUAGUA CU    92

(2) INFORMATION FOR SEQ ID NO:4:

(i) SEQUENCE CHARACTERISTICS:
        (A) LENGTH: 185 base pairs
        (B) TYPE: nucleic acid
        (C) STRANDEDNESS: single
        (D) TOPOLOGY: linear (ii) MOLECULE TYPE: RNA (genomic)

(iii) HYPOTHETICAL: NO (vi) ORIGINAL SOURCE:
        (A) ORGANISM: Human immunodeficiency virus type 1

(xi) SEQUENCE DESCRIPTION: SEQ ID NO:4:

GGUGAAAUUG CUGCCAUUGA GAUCUAGAGC ACGGGCUAGC GCUUUCGCGC UCUCCCAGGU    60

GACGCCUCGU GAAGAGGCGC GACCUUCGUG CGUUUCGGUG ACGCACGAGA ACCGCCACGC    120

UGCUUCGCAG CGUGGCUCCU UCGCGCAGCC CGCUGCGCGA GGUGACCCCC CGAAGGGGGG    180

UUCCC    185